US011206988B2

United States Patent
Goldshtein et al.

(10) Patent No.: US 11,206,988 B2
(45) Date of Patent: Dec. 28, 2021

(54) POWER-EFFICIENT PRESSURE-SENSOR IMPLANT

(71) Applicant: VECTORIOUS MEDICAL TECHNOLOGIES LTD., Tel-Aviv (IL)

(72) Inventors: Oren Goldshtein, Nahariya (IL); Tal Azaria, Ashdod (IL); Aharon Daffan, Jerusalem (IL); Yair Levi, Haifa (IL)

(73) Assignee: VECTORIOUS MEDICAL TECHNOLOGIES LTD., Tel Aviv (IL)

( * ) Notice: Subject to any disclaimer, the term of this patent is extended or adjusted under 35 U.S.C. 154(b) by 453 days.

(21) Appl. No.: 16/066,690

(22) PCT Filed: Dec. 30, 2015

(86) PCT No.: PCT/IB2015/060054
§ 371 (c)(1),
(2) Date: Jun. 28, 2018

(87) PCT Pub. No.: WO2017/115112
PCT Pub. Date: Jul. 6, 2017

(65) Prior Publication Data
US 2019/0008401 A1 Jan. 10, 2019

(51) Int. Cl.
*A61B 5/0215* (2006.01)
*H02J 50/80* (2016.01)
(Continued)

(52) U.S. Cl.
CPC ........ *A61B 5/02156* (2013.01); *A61B 5/0031* (2013.01); *A61B 5/021* (2013.01);
(Continued)

(58) Field of Classification Search
CPC ... A61B 5/02156; A61B 5/076; A61B 5/0215; A61B 5/021; A61B 5/7225;
(Continued)

(56) References Cited

U.S. PATENT DOCUMENTS 3,264,861 A    8/1966   Miles
4,127,110 A   11/1978   Bullara
(Continued)

FOREIGN PATENT DOCUMENTS

JP          S5973747 A    4/1984
KR   20040060577 A    7/2004
(Continued)

OTHER PUBLICATIONS

Bradford et al., "Wireless Power and Data Transmission for a Pressure Sensing Medical Implant", Proceedings BMT 2010, Rostock, Germany, 4 pages, Oct. 6-8, 2010.
(Continued)

*Primary Examiner* — Devin B Henson
*Assistant Examiner* — Justin Xu
(74) *Attorney, Agent, or Firm* — Kligler & Associates Patent Attorneys Ltd (57) ABSTRACT

Apparatus and methods are described, including apparatus that includes an antenna (34), configured to, by drawing energy from a magnetic field, provide a main supply voltage. The apparatus further includes operational circuitry (46, 22) configured to operate only if a derived supply voltage, derived from the main supply voltage and supplied to the operational circuitry, is greater than a threshold value, and modulating circuitry (36, 40, 42), configured to modulate a load of the antenna by alternatingly (i) connecting current-drawing circuitry to the main supply voltage, thus causing the main supply voltage to drop below the threshold value, and (ii) disconnecting the current-drawing circuitry from the
(Continued)

main supply voltage without disconnecting the operational circuitry from the main supply voltage. Other embodiments are also described.

10 Claims, 6 Drawing Sheets

(51) Int. Cl.
| | |
|---|---|
| A61B 5/07 | (2006.01) |
| A61B 5/021 | (2006.01) |
| A61B 5/00 | (2006.01) |
| H02J 50/12 | (2016.01) |
| H04B 5/00 | (2006.01) |
| H02J 7/00 | (2006.01) |
| H02J 50/10 | (2016.01) |

(52) U.S. Cl.
CPC ............ *A61B 5/0215* (2013.01); *A61B 5/076* (2013.01); *A61B 5/6869* (2013.01); *A61B 5/7225* (2013.01); *H02J 50/12* (2016.02); *H02J 50/80* (2016.02); *H04B 5/0031* (2013.01); *H04B 5/0043* (2013.01); *A61B 2560/0219* (2013.01); *A61B 2560/0223* (2013.01); *A61B 2560/0252* (2013.01); *A61B 2562/0247* (2013.01); *A61B 2562/0271* (2013.01); *H02J 7/00034* (2020.01); *H02J 50/10* (2016.02)

(58) Field of Classification Search
CPC ................ A61B 5/6869; A61B 5/0031; A61B 2560/0219; A61B 2562/0271; A61B 2560/0223; A61B 2560/0252; A61B 2562/0247; H02J 50/80; H02J 50/12; H02J 7/00034; H02J 50/10; H04B 5/0031; H04B 5/0043
See application file for complete search history.

(56) References Cited

U.S. PATENT DOCUMENTS

| | | | |
|---|---|---|---|
| 4,206,761 A | 6/1980 | Cosman | |
| 4,237,900 A | 12/1980 | Schulman et al. | |
| 4,256,094 A | 3/1981 | Kapp et al. | |
| 4,377,851 A | 3/1983 | McNamara | |
| 4,432,372 A | 2/1984 | Monroe | |
| 4,519,401 A | 5/1985 | Ko et al. | |
| 4,669,485 A * | 6/1987 | Russell | A61B 5/021 |
| | | | 600/492 |
| 4,743,836 A | 5/1988 | Grzybowski et al. | |
| 4,791,934 A | 12/1988 | Brunnett | |
| 4,881,939 A | 11/1989 | Newman | |
| 5,105,190 A | 4/1992 | Kip et al. | |
| 5,113,868 A | 5/1992 | Wise et al. | |
| 5,300,093 A * | 4/1994 | Koestner | A61N 1/36521 |
| | | | 607/32 |
| 5,480,412 A | 1/1996 | Mouchawar et al. | |
| 5,493,470 A | 2/1996 | Zavracky et al. | |
| 5,514,171 A | 5/1996 | Hoegnelid et al. | |
| 5,549,646 A | 8/1996 | Katz et al. | |
| 5,564,434 A | 10/1996 | Halperin et al. | |
| 5,942,692 A | 4/1999 | Haase et al. | |
| 6,015,386 A | 1/2000 | Kensey et al. | |
| 6,025,725 A | 2/2000 | Gershenfeld et al. | |
| 6,051,853 A | 4/2000 | Shimada et al. | |
| 6,111,520 A | 8/2000 | Allen et al. | |
| 6,113,553 A | 9/2000 | Chubbuck | |
| 6,171,252 B1 | 1/2001 | Roberts | |
| 6,275,681 B1 | 8/2001 | Vega et al. | |
| 6,309,350 B1 | 10/2001 | Vantassel et al. | |
| 6,389,371 B1 | 5/2002 | Tsuchiya et al. | |
| 6,409,674 B1 | 6/2002 | Brockway et al. | |
| 6,622,041 B2 | 9/2003 | Terry, Jr. et al. | |
| 6,667,725 B1 | 12/2003 | Simons et al. | |
| 6,772,070 B2 | 8/2004 | Gilmanshin et al. | |
| 6,778,070 B1 | 8/2004 | Thomas | |
| 6,926,670 B2 | 8/2005 | Rich et al. | |
| 6,936,053 B1 | 8/2005 | Weiss | |
| 7,086,270 B2 | 8/2006 | Weinberg et al. | |
| 7,149,587 B2 | 12/2006 | Wardle et al. | |
| 7,216,048 B2 | 5/2007 | Wang et al. | |
| 7,256,695 B2 | 8/2007 | Hamel et al. | |
| 7,317,951 B2 | 1/2008 | Schneider et al. | |
| 7,335,161 B2 | 2/2008 | Von Arx et al. | |
| 7,413,547 B1 | 8/2008 | Lichtscheidl et al. | |
| 7,425,749 B2 | 9/2008 | Hartzell et al. | |
| 7,509,169 B2 | 3/2009 | Eigler et al. | |
| 7,515,971 B1 | 4/2009 | Doan | |
| 7,628,054 B2 | 12/2009 | Hajishah et al. | |
| 7,634,319 B2 | 12/2009 | Schneider et al. | |
| 7,635,338 B2 | 12/2009 | Eide | |
| 7,647,831 B2 | 1/2010 | Corcoran et al. | |
| 7,677,107 B2 | 3/2010 | Nunez et al. | |
| 7,678,123 B2 | 3/2010 | Chanduszko | |
| 7,684,872 B2 | 3/2010 | Carney et al. | |
| 7,686,768 B2 | 3/2010 | Bodecker et al. | |
| 7,762,138 B2 | 7/2010 | Zdeblick et al. | |
| 7,860,579 B2 | 12/2010 | Goetzinger et al. | |
| 7,899,550 B1 | 3/2011 | Doan et al. | |
| 8,021,307 B2 | 9/2011 | White et al. | |
| 8,118,749 B2 | 2/2012 | White et al. | |
| 8,154,389 B2 | 4/2012 | Rowland et al. | |
| 8,285,204 B2 | 10/2012 | Martin | |
| 8,353,841 B2 | 1/2013 | White et al. | |
| 8,355,777 B2 | 1/2013 | White et al. | |
| 8,406,358 B1 | 3/2013 | Uehara et al. | |
| 8,432,265 B2 | 4/2013 | Rowland et al. | |
| 8,493,187 B2 | 7/2013 | Rowland et al. | |
| 8,810,405 B2 | 8/2014 | Stevenson et al. | |
| 8,894,582 B2 | 11/2014 | Nunez et al. | |
| 9,513,609 B2 | 12/2016 | Thueringer et al. | |
| 9,662,066 B2 | 5/2017 | Ledet et al. | |
| 9,730,764 B2 | 8/2017 | Weide et al. | |
| 2001/0018596 A1 | 8/2001 | Selmon et al. | |
| 2002/0045921 A1 | 4/2002 | Wolinsky et al. | |
| 2002/0077556 A1 | 6/2002 | Schwartz | |
| 2002/0120200 A1 | 8/2002 | Brockway et al. | |
| 2003/0045781 A1 * | 3/2003 | Rosenheimer | A61B 5/7445 |
| | | | 600/300 |
| 2003/0097073 A1 | 5/2003 | Bullister et al. | |
| 2003/0139677 A1 | 7/2003 | Fonseca et al. | |
| 2004/0103906 A1 | 6/2004 | Schulman et al. | |
| 2004/0158167 A1 | 8/2004 | Smith et al. | |
| 2005/0004644 A1 | 1/2005 | Kelsch et al. | |
| 2005/0065589 A1 | 3/2005 | Schneider et al. | |
| 2005/0088184 A1 | 4/2005 | Burdick et al. | |
| 2005/0288596 A1 | 12/2005 | Eigler et al. | |
| 2006/0116572 A1 | 6/2006 | Case | |
| 2006/0161364 A1 | 7/2006 | Wang et al. | |
| 2006/0206178 A1 | 9/2006 | Kim | |
| 2006/0229488 A1 | 10/2006 | Ayre et al. | |
| 2006/0287602 A1 | 12/2006 | O'Brien et al. | |
| 2007/0049980 A1 | 3/2007 | Zielinski et al. | |
| 2007/0049984 A1 | 3/2007 | Osypka | |
| 2007/0118038 A1 | 5/2007 | Bodecker et al. | |
| 2007/0135826 A1 | 6/2007 | Zaver et al. | |
| 2007/0142727 A1 | 6/2007 | Zhang et al. | |
| 2007/0179583 A1 | 8/2007 | Goetzinger et al. | |
| 2007/0255144 A1 | 11/2007 | Tulkki et al. | |
| 2007/0261496 A1 | 11/2007 | Jonsson et al. | |
| 2007/0293779 A1 | 12/2007 | Bardy | |
| 2008/0004673 A1 | 1/2008 | Rossing et al. | |
| 2008/0033527 A1 | 2/2008 | Nunez et al. | |
| 2008/0045242 A1 | 2/2008 | Dekock et al. | |
| 2008/0064966 A1 | 3/2008 | Brockway et al. | |
| 2008/0092663 A1 | 4/2008 | Corcoran et al. | |
| 2008/0139959 A1 | 6/2008 | Miethke et al. | |
| 2008/0154101 A1 | 6/2008 | Jain et al. | |
| 2008/0227487 A1 | 9/2008 | Daniels et al. | |
| 2008/0269573 A1 | 10/2008 | Najafi et al. | |
| 2008/0281212 A1 | 11/2008 | Nunez et al. | |

(56) References Cited

U.S. PATENT DOCUMENTS

| | | |
|---|---|---|
| 2009/0005859 A1 | 1/2009 | Keilman |
| 2009/0013791 A1 | 1/2009 | Zdeblick et al. |
| 2009/0024042 A1 | 1/2009 | Nunez et al. |
| 2009/0030291 A1 | 1/2009 | O'Brien et al. |
| 2009/0036754 A1 | 2/2009 | Pons et al. |
| 2009/0069648 A1 | 3/2009 | Irazogui et al. |
| 2009/0093729 A1 | 4/2009 | Zhang et al. |
| 2009/0192381 A1 | 7/2009 | Brockway et al. |
| 2009/0275924 A1 | 11/2009 | Lattanzio et al. |
| 2009/0281520 A1 | 11/2009 | Highley et al. |
| 2009/0299216 A1 | 12/2009 | Chen et al. |
| 2010/0179449 A1 | 7/2010 | Chow et al. |
| 2010/0179618 A1 | 7/2010 | Marnfeldt et al. |
| 2010/0249756 A1 | 9/2010 | Koh |
| 2010/0280330 A1 | 11/2010 | Samuelsson et al. |
| 2011/0021887 A1 | 1/2011 | Crivelli et al. |
| 2011/0040206 A1 | 2/2011 | Burger et al. |
| 2011/0043336 A1 | 2/2011 | Gueorguiev |
| 2011/0066046 A1* | 3/2011 | Young ............... A61B 5/02241 600/486 |
| 2011/0133894 A1 | 6/2011 | Henning et al. |
| 2011/0160560 A1 | 6/2011 | Stone |
| 2011/0264217 A1 | 10/2011 | Qureshi |
| 2011/0303229 A1 | 12/2011 | Najafi et al. |
| 2012/0022507 A1 | 1/2012 | Najafi et al. |
| 2012/0319862 A1 | 12/2012 | Nagy et al. |
| 2013/0107913 A1 | 5/2013 | Savoj |
| 2013/0215979 A1 | 8/2013 | Yakovlev et al. |
| 2013/0222153 A1 | 8/2013 | Rowland et al. |
| 2013/0233086 A1 | 9/2013 | Besling et al. |
| 2014/0028467 A1 | 1/2014 | Nagy et al. |
| 2014/0062717 A1 | 3/2014 | Mudumbai et al. |
| 2014/0155710 A1 | 6/2014 | Rowland et al. |
| 2014/0306807 A1 | 10/2014 | Rowland et al. |
| 2015/0282720 A1 | 10/2015 | Goldshtein et al. |
| 2015/0290465 A1 | 10/2015 | Mashiach |
| 2016/0022216 A1 | 1/2016 | Goldshtein et al. |
| 2016/0058324 A1 | 3/2016 | Cao et al. |
| 2017/0018172 A1 | 1/2017 | He et al. |
| 2017/0118543 A1 | 4/2017 | Ha et al. |
| 2017/0155429 A1 | 6/2017 | Hung et al. |

FOREIGN PATENT DOCUMENTS

| | | |
|---|---|---|
| WO | 2006042280 A2 | 4/2006 |
| WO | 2008042229 A2 | 4/2008 |
| WO | 2008127525 A1 | 10/2008 |
| WO | 2009097485 A1 | 8/2009 |
| WO | 2011053246 A1 | 5/2011 |
| WO | 2012078861 A2 | 6/2012 |
| WO | 2012090206 A2 | 7/2012 |
| WO | 2014006471 A2 | 1/2014 |
| WO | 2014145012 A2 | 9/2014 |
| WO | 2014170771 A1 | 10/2014 |

OTHER PUBLICATIONS

Dai et al., "Capacitive Micro Pressure Sensor Integrated with a Ring Oscillator Circuit on Chip", Sensors 2009, vol. 9, chapter 12, pp. 10158-10170, Jan. 1, 2009.

Yameogo et al., "Self Calibrating pressure sensor for biomedical applications", IEEE Sensors Conference, pp. 691-694, Oct. 25-28, 2009.

Mandal et al., "Power-Efficient Impedance-Modulation Wireless Data Links for Biomedical Implants", IEEE Transactions on Biomedical Circuits and Systems, vol. 2, No. 4, pp. 301-315, Dec. 4, 2008.

Olivo et al., "Electronic implants: Power delivery and management", Integrated Systems Laboratory—EPFL, 6 pages, Mar. 22, 2013.

Ziaie et al., "An Implantable Microsystem for Tonometric Blood Pressure Measurement", Biomedical Microdevices, vol. 3, Issue 4, pp. 285-292, Dec. 2001.

Hershko et al., U.S. Appl. No. 15/981,914, filed May 17, 2018.

U.S. Appl. No. 14/437,198 office action dated Jan. 4, 2019.

U.S. Appl. No. 14/437,198 office action dated Jul. 31, 2019.

Cleven et al., "A Novel Fully Implantable Wireless Sensor System for Monitoring Hypertension Patients", IEEE Transactions on Biomedical Engineering vol. 59, No. 11, pp. 3124-3130, Nov. 2012.

Jiang., "Design challenges of implantable pressure monitoring system", Frontiers of Neuroscience, vol. 4, Art 29, pp. 1-4, Feb. 26, 2010.

Simons et al., "Spiral chip implantable radiator and printed loop external receptor for RF telemetry in bio-sensor systems", In Radion and Wireless Conference IEEE, 12 pages, 2004.

Simons et al., "Wearable wireless telemetry system for implantable bio-MEMS sensors", In Engineering in Medicine and Biology Society Conference, IEEE, 12 pages, 2006.

Maxim, "Approaches for Compensating Span and Offset in Pressure Sensors", Application Note 743, 5 pages, Mar. 27, 2001.

Coosemans., "An autonomous bladder pressure monitoring system", Katholike Universiteit Leuven, Department ESAT-MICAS, Kasteelpark Arenberg, Belgium, Sensorsand Actuators A: Physical, Elsevier BV, vol. 123-124, pp. 155-161, Sep. 23, 2005.

\* cited by examiner

POWER-EFFICIENT PRESSURE-SENSOR IMPLANT

FIELD OF THE INVENTION

Embodiments of the present relate generally to pressure-sensor implants, e.g., for sensing intracardiac pressure.

BACKGROUND

Some subjects may chronically suffer from abnormal intracardiac pressures. In some cases, intervention may be needed to treat such subjects.

WO 2014/076620, whose disclosure is incorporated herein by reference, describes a method that includes, in a living organ in which an ambient pressure varies as a function of time, sensing the ambient pressure using a pressure sensor. The pressure sensor has a capacitance that varies in response to the ambient pressure, so as to produce a time-varying waveform. A calibration voltage, which modifies the capacitance and thus the time-varying waveform, is applied to the pressure sensor. The time-varying waveform is processed so as to isolate and measure a contribution of the calibration voltage to the waveform. A dependence of the capacitance on the ambient pressure is calibrated using the measured contribution of the calibration voltage.

WO 2014/170771, whose disclosure is incorporated herein by reference, describes an implant that includes an antenna unit and an encapsulation. The antenna unit includes an elongated ferrite core having a first length and an antenna coil wound around the ferrite core, and is configured to communicate with an external unit using inductive coupling of a magnetic field. The encapsulation encapsulates the antenna unit, and includes one or more openings that are aligned with the ferrite core and have respective second lengths that are equal to or greater than the first length of the ferrite core.

U.S. Pat. No. 6,051,853, whose disclosure is incorporated herein by reference, describes a semiconductor pressure sensor utilizing electrostatic capacitance that has a plurality of pressure sensing electrostatic capacitances and a reference electrostatic capacitance formed on one side of a silicon chip. As a movable electrode, the pressure sensing electrostatic capacitances each have a diaphragm, which may have a displacement portion composed of a central area thereof, and a peripheral portion which is more deformable than the central portion.

SUMMARY OF THE INVENTION

There is provided, in accordance with some embodiments of the present invention, apparatus that includes an antenna configured to, by drawing energy from a magnetic field, provide a main supply voltage. The apparatus further includes (a) operational circuitry configured to operate only if a derived supply voltage, derived from the main supply voltage and supplied to the operational circuitry, is greater than a threshold value, and (b) modulating circuitry, configured to modulate a load of the antenna by alternatingly (i) connecting current-drawing circuitry to the main supply voltage, thus causing the main supply voltage to drop below the threshold value, and (ii) disconnecting the current-drawing circuitry from the main supply voltage without disconnecting the operational circuitry from the main supply voltage.

In some embodiments, the apparatus further includes circuitry configured to reduce variations in the main supply voltage that are caused by variations in an amount of current drawn by the current-drawing circuitry, by drawing an amount of current that varies inversely with the amount of current drawn by the current-drawing circuitry.

In some embodiments, the current-drawing circuitry includes at least part of the modulating circuitry.

In some embodiments, the modulating circuitry includes a switch, and is configured to connect the current-drawing circuitry to the main supply voltage by closing the switch.

In some embodiments, the apparatus further includes a backup voltage source, configured to:

when the current-drawing circuitry is disconnected from the main supply voltage, derive a backup voltage from the main supply voltage, and when the current-drawing circuitry is connected to the main supply voltage, supply the backup voltage to the operational circuitry, thus maintaining operation of the operational circuitry.

In some embodiments, the backup voltage source is a first backup voltage source, the backup voltage is a first backup voltage, and the apparatus further includes a second backup voltage source, configured to:

when the current-drawing circuitry is connected to the main supply voltage, derive a second backup voltage from the main supply voltage, and when the current-drawing circuitry is disconnected from the main supply voltage, supply the second backup voltage to the current-drawing circuitry.

In some embodiments, the operational circuitry includes a sensor configured to sense a parameter, the modulating circuitry being configured to modulate the load of the antenna in response to sensing of the sensor.

In some embodiments, the apparatus includes an implant that includes the antenna, the sensor, and the modulating circuitry, the implant being for use with an external unit configured to generate the magnetic field.

In some embodiments, the apparatus further includes the external unit.

In some embodiments, the external unit is configured to compute, based on modulations of the load of the antenna, the value of the parameter.

In some embodiments, the sensor includes a pressure sensor, and the parameter includes an ambient pressure.

In some embodiments, the pressure sensor includes a capacitive pressure sensor having a capacitance that varies in response to the ambient pressure.

In some embodiments, the apparatus further includes conversion circuitry configured to generate an output having a property that is a function of the capacitance of the capacitive pressure sensor, wherein the modulating circuitry is configured to modulate the load of the antenna in response to the output.

In some embodiments, a frequency of the output of the conversion circuitry is a function of the capacitance of the capacitive pressure sensor.

In some embodiments, the main supply voltage is less than 5 V when the current-drawing circuitry is connected to the main supply voltage.

In some embodiments, the main supply voltage is less than 22 V when the current-drawing circuitry is disconnected from the main supply voltage.

There is further provided, in accordance with some embodiments of the present invention, a method for modulating a load of an antenna. By using an antenna to draw energy from a magnetic field, a main supply voltage is provided. A derived supply voltage is derived from the main supply voltage, and supplied to operational circuitry that is configured to operate only if the derived supply voltage is greater than a threshold value. The load of the antenna is modulated by alternatingly (i) connecting current-drawing circuitry to the main supply voltage, thus causing the main supply voltage to drop below the threshold value, and (ii) disconnecting the current-drawing circuitry from the main supply voltage without disconnecting the operational circuitry from the main supply voltage.

There is further provided, in accordance with some embodiments of the present invention, apparatus including a sensor, configured to vary a capacitance of the sensor in response to a parameter. The apparatus further includes (a) conversion circuitry, configured to convert an input capacitance into an output that is indicative of the input capacitance, (b) a set of calibration capacitors, (c) a first switching unit having multiple first-switching-unit settings that (i) connect respective subsets of the calibration capacitors to the conversion circuitry, and further (ii) have respective first-switching-unit effects on the output, and (d) a second switching unit connected to the sensor and having multiple second-switching-unit settings that (i) connect the sensor to the conversion circuitry, and further (ii) have respective second-switching-unit effects on the output that are the same as the first-switching-unit effects.

In some embodiments, the conversion circuitry is configured to convert the input capacitance into an output-signal frequency that is indicative of the input capacitance.

In some embodiments, the sensor is configured to vary the capacitance of the sensor in response to an ambient pressure.

In some embodiments, the apparatus further includes circuitry configured to:

by setting the first switching unit to each of the first-switching-unit settings, drive the conversion circuitry to generate multiple calibration outputs, and subsequently, by setting the second switching unit to one or more of the second-switching-unit settings, drive the conversion circuitry to generate one or more sensing outputs, the calibration outputs and the sensing outputs being collectively indicative of the capacitance of the sensor.

In some embodiments, the circuitry is further configured to:

ascertain a correspondence between the calibration outputs and the first-switching-unit settings, and compute the capacitance of the sensor, based on the sensing outputs and the correspondence.

In some embodiments, the circuitry is configured to compute the capacitance of the sensor by repeatedly setting the second switching unit to another one of the second-switching-unit settings, until (i) the sensing output from the conversion circuitry converges to a particular one of the calibration outputs, and (ii) per the correspondence, the particular calibration output corresponds to a current setting of the second switching unit.

In some embodiments, the apparatus further includes:

a reference capacitor configured not to vary a capacitance of the reference capacitor in response to the parameter; and a third switching unit connected to the reference capacitor and having multiple third-switching-unit settings that (i) connect the reference capacitor to the conversion circuitry, and further (ii) have respective third-switching-unit effects on the output that are the same as the first-switching-unit effects.

There is further provided, in accordance with some embodiments of the present invention, a method for computing a capacitance of a sensor. The method includes providing (a) conversion circuitry, configured to convert an input capacitance into an output that is indicative of the input capacitance, (b) a set of calibration capacitors, (c) a first switching unit having multiple first-switching-unit settings that (i) connect respective subsets of the calibration capacitors to the conversion circuitry, and further (ii) have respective first-switching-unit effects on the output, and (d) a second switching unit connected to a sensor and having multiple second-switching-unit settings that (i) connect the sensor to the conversion circuitry, and further (ii) have respective second-switching-unit effects on the output that are the same as the first-switching-unit effects. By setting the first switching unit to each of the first-switching-unit settings, the conversion circuitry is driven to generate multiple calibration outputs. Subsequently, by setting the second switching unit to one or more of the second-switching-unit settings, the conversion circuitry is driven to generate one or more sensing outputs. A correspondence between the calibration outputs and the first-switching-unit settings is ascertained. The capacitance of the sensor is computed, based on the sensing outputs and the correspondence.

In some embodiments, the sensor is configured to vary a capacitance of the sensor in response to a parameter, and the method further includes:

providing (a) a reference capacitor configured not to vary a capacitance of the reference capacitor in response to the parameter, and (b) a third switching unit connected to the reference capacitor and having multiple third-switching-unit settings that (i) connect the reference capacitor to the conversion circuitry, and further (ii) have respective third-switching-unit effects on the output that are the same as the first-switching-unit effects, by setting the third switching unit to one or more of the third-switching-unit settings, driving the conversion circuitry to generate one or more reference outputs;

in response to the reference outputs, computing the capacitance of the reference capacitor; and based on the capacitance of the reference capacitor and the capacitance of the sensor, computing a value of the parameter.

There is further provided, in accordance with some embodiments of the present invention, a method for forming capacitors. A sensing capacitor is formed from a first portion of a wafer, the sensing capacitor having at least one terminal that is sensitive to an ambient pressure. A first set of electrical connections is connected to the sensing capacitor. A reference capacitor is formed from a second portion of the wafer that is adjacent to the first portion, the reference capacitor not having any terminal that is sensitive to the ambient pressure. A second set of electrical connections that is identical to the first set is connected to the reference capacitor.

In some embodiments, the method further includes implanting the sensing capacitor and the reference capacitor in a subject.

In some embodiments, implanting the sensing capacitor and the reference capacitor in the subject includes implanting the sensing capacitor and the reference capacitor in a heart of the subject.

In some embodiments, the method further includes separating the sensing capacitor and the reference capacitor from one another.

In some embodiments, forming the sensing capacitor and the reference capacitor includes forming the sensing capacitor and reference capacitor such that one or more portions of the sensing capacitor protrude into the reference capacitor.

In some embodiments, forming the sensing capacitor and the reference capacitor includes forming the sensing capacitor and reference capacitor such that one or more portions of the reference capacitor protrude into the sensing capacitor.

In some embodiments, forming the sensing capacitor and the reference capacitor includes forming the sensing capacitor and reference capacitor such that the protruding portions of the reference capacitor are interleaved with portions of the sensing capacitor.

There is further provided, in accordance with some embodiments of the present invention, apparatus that includes a sensing capacitor formed from a first portion of a wafer, the sensing capacitor having at least one terminal that is sensitive to an ambient pressure. The apparatus further includes (i) a first set of electrical connections connected to the sensing capacitor, (ii) a reference capacitor formed from a second portion of the wafer that is adjacent to the first portion, the reference capacitor not having any terminal that is sensitive to the ambient pressure, and (iii) a second set of electrical connections, which is identical to the first set, connected to the reference capacitor.

In some embodiments, the sensing capacitor and the reference capacitor are detached from one another.

There is further provided, in accordance with some embodiments of the present invention, a method for ascertaining an unknown ambient pressure, using a pressure sensor.

First, a calibration of the pressure sensor is performed, using one or more known input capacitances. For each input capacitance of the one or more known input capacitances, for each ambient temperature of a plurality of controlled ambient temperatures, a respective first calibration output of conversion circuitry that is output responsively to the input capacitance is measured. For each ambient temperature of the plurality of controlled ambient temperatures, for each ambient pressure of a plurality of controlled ambient pressures, a respective second calibration output of the conversion circuitry that is output responsively to input from the pressure sensor is measured. Subsequently, the unknown ambient pressure is ascertained, based on the first calibration outputs, the second calibration outputs, a measured ambient temperature, a first real-time output of the conversion circuitry that is output responsively to a given one of the known input capacitances, and a second real-time output of the conversion circuitry that is output responsively to an input from the pressure sensor.

In some embodiments,
 a first switching unit connects the conversion circuitry to a set of calibration capacitors and has a plurality of settings,
 a second switching unit connects the conversion circuitry to the pressure sensor and has at least some of the settings of the first switching unit, and
 the method further includes:
  measuring the first real-time output, by setting the first switching unit to a given one of the settings, and
  measuring the second real-time output, by setting the second switching unit to the given one of the settings.

In some embodiments,
 performing the calibration further includes, for each input capacitance, for each ambient pressure, for each ambient temperature, computing a calibration ratio between (i) one of the first calibration outputs that was measured for the input capacitance and the ambient temperature, and (ii) one of the second calibration outputs that was measured for the ambient pressure and the ambient temperature, and ascertaining the unknown ambient pressure includes:
 computing a real-time ratio between the first real-time output and second real-time output, and
 ascertaining the unknown ambient pressure, by comparing the real-time ratio to the calibration ratios that were computed for the given one of the known input capacitances.

In some embodiments, the method further includes selecting the given one of the known input capacitances in response to comparing (i) one or more first pre-real-time outputs of the conversion circuitry that are output responsively to respective inputs from the pressure sensor to, respectively, (ii) one or more second pre-real-time outputs of the conversion circuitry that are output responsively to respective ones of the known input capacitances.

There is further provided, in accordance with some embodiments of the present invention, apparatus that includes a pressure sensor, conversion circuitry, and control circuitry. The control circuitry is configured to perform a calibration of the pressure sensor using one or more known input capacitances, by, (i) for each input capacitance of the one or more known input capacitances, for each ambient temperature of a plurality of controlled ambient temperatures, measuring a respective first calibration output of the conversion circuitry that is output responsively to the input capacitance, and (ii) for each ambient temperature of the plurality of controlled ambient temperatures, for each ambient pressure of a plurality of controlled ambient pressures, measuring a respective second calibration output of the conversion circuitry that is output responsively to input from the pressure sensor. The control circuitry is further configured to subsequently ascertain an unknown ambient pressure, based on the first calibration outputs, the second calibration outputs, a measured ambient temperature, a first real-time output of the conversion circuitry that is output responsively to a given one of the known input capacitances, and a second real-time output of the conversion circuitry that is output responsively to an input from the pressure sensor.

The present invention will be more fully understood from the following detailed description of embodiments thereof, taken together with the drawings, in which:

DETAILED DESCRIPTION OF EMBODIMENTS

Overview

Embodiments of the present invention provide an implant comprising a capacitive pressure sensor (or "sensing capacitor"), an antenna, and other circuitry. The implant may be implanted, for example, in a subject's heart. The implant is powered, via electromagnetic inductive coupling, by an external unit. That is, the external unit provides a magnetic field, and the antenna of the implant, by drawing energy from the magnetic field, provides a main supply voltage that supplies the implant. In response to an output from the sensor, the load of the antenna of the implant is modulated, by alternatingly connecting and disconnecting a logic processing unit (LPU) from the main supply voltage, in a manner that is indicative of the ambient pressure sensed by the sensor. The modulation is sensed by the external unit as temporal variations in the amount of magnetic-field energy consumed by the implant. In response to sensing the temporal variations, the external unit computes the ambient pressure sensed by the sensor.

It is possible to implement the above-described scheme by placing a modulation switch between the antenna and both (i) the sensor, and (ii) the LPU. A problem with this implementation, however, is that the sensor typically requires a relatively high amount of voltage to operate. Hence, while the switch is closed (and hence, the antenna is loaded), the antenna would need to supply sufficient voltage to maintain operation of the sensor, as well as to provide sufficient backup voltage to supply the sensor while the switch is open. The antenna would thus need to be supplied with a relatively large amount of energy. Moreover, the LPU, which typically consumes a relatively large amount of current but does need such a high voltage, would consume a relatively large amount of excess energy.

Embodiments described herein provide a superior solution, whereby the LPU is alternatingly connected to and disconnected from the main supply voltage, but the sensor remains connected to the main supply voltage. In other words, the modulation switch is placed between the antenna and the LPU, but not between the antenna and the sensor. This solution allows the main supply voltage to be lower than in the above-described inferior implementation. Moreover, this solution provides for sufficient variations in the antenna load, or "modulation depth," such that the modulation may be properly detected by the external unit.

In some embodiments, the implant comprises a converter configured to generate an output signal having a frequency that is a function of the capacitance of the capacitive pressure sensor, and the load of the antenna is modulated in response to the output signal. For such embodiments, it may be desirable to learn the "input-capacitance-to-output-frequency" mapping of the converter, such that the capacitance of the sensor may be accurately computed from the output signal. Hence, embodiments of the present invention further provide a calibration procedure that facilitates the learning of this mapping. For the calibration procedure, a set of calibration capacitors is provided, along with a first switching unit that has multiple first-switching-unit settings. Each of the settings connects a respective subset of the calibration capacitors to the converter. Hence, by varying the setting of the first switching unit, various input capacitances may be obtained. For each input capacitance, the frequency of the output signal from the converter is recorded, such that the input-capacitance-to-output-frequency mapping of the converter is obtained. Subsequently, the inverse of the mapping may be used to compute the capacitance of the sensor, given the output of the converter.

A challenge inherent in using the above calibration technique is that each of the first-switching-unit settings has a different respective effect on the output of the converter. For example, the resistance of the first switching unit may vary, depending on the selected setting of the switching unit, such that the respective outputs observed during calibration are a function not only of the respective input capacitances, but also of the respective "input resistances" provided by the first switching unit. Embodiments of the present invention address the above challenge, by providing a second switching unit, connected to the sensor that is effectively a duplicate of the first switching unit. By controlling the second switching unit, the input resistance provided by the second switching unit may be "matched" to an input resistance provided by the first switching unit during calibration, thus allowing the capacitance of the sensor to be accurately computed from the output of the converter.

Typically, the implant further comprises a reference capacitor, the capacitance of which does not vary in response to the ambient pressure. The reference capacitor is formed adjacent to the sensing capacitor, on a shared wafer, and the respective sets of electrical connections connected to the two capacitors are identical to one another. This allows the reference capacitor to have properties very similar to those of the sensing capacitor, such that the reference capacitor and sensing capacitor are affected by various factors other than pressure (e.g., age, radiofrequency noise, etc.) in the same way. Hence, the reference capacitor allows for compensating for such factors, thus allowing for a more accurate computation of the intracardiac pressure.

System Description

Figure 1:
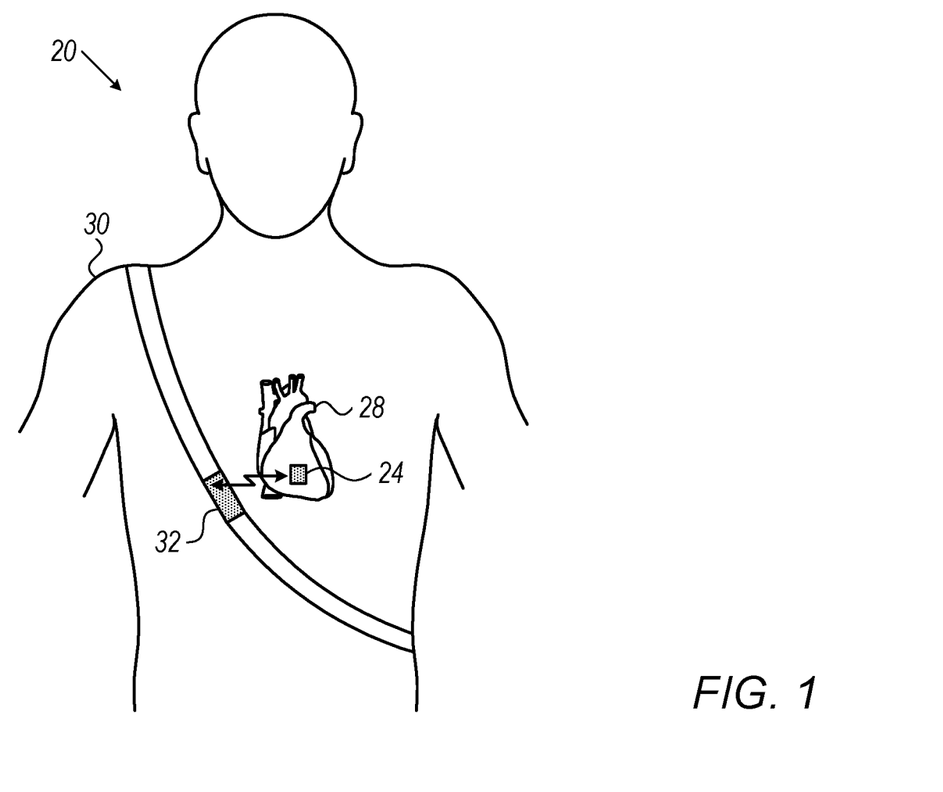
FIG. 1 is a schematic illustration of an implant and an external unit, in accordance with some embodiments of the present invention.

Reference is initially made to FIG. 1, which is a schematic illustration of apparatus 20 comprising an implant 24 and an external unit 32, in accordance with some embodiments of the present invention. As shown in FIG. 1, implant 24 may be implanted in the heart 28 of a subject 30, e.g., within the left atrium of heart 28. As described hereinabove, external unit 32 wirelessly supplies power to implant 24, and the implant provides feedback to the external unit. An apparatus of this sort is described, for example, in PCT International Publications WO 2014/076620 and WO 2014/170771, which are both assigned to the assignee of the present patent application and whose disclosures are incorporated herein by reference.

Figure 2:
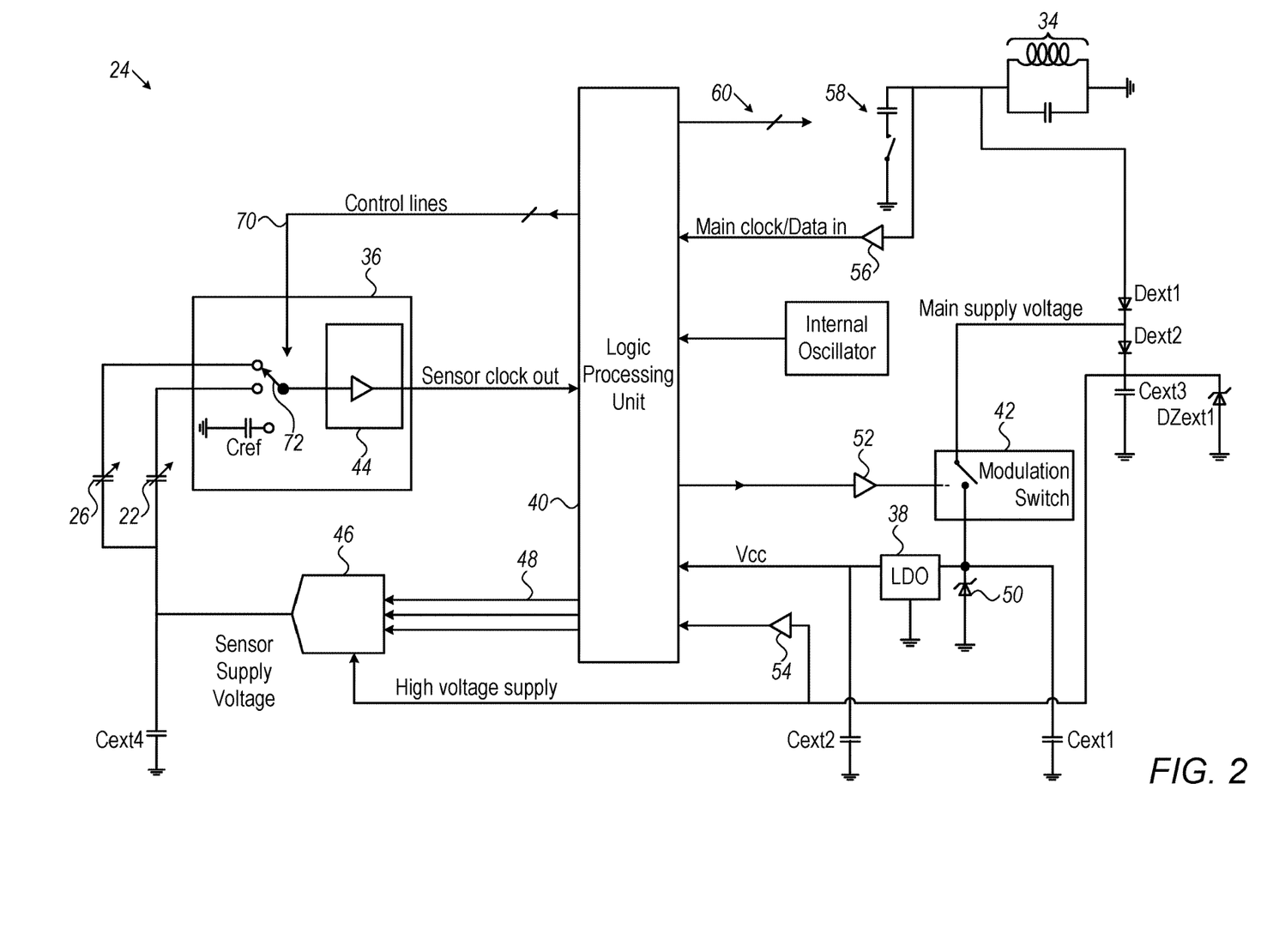
FIG. 2 is a block diagram showing circuitry contained inside the implant of FIG. 1, in accordance with some embodiments of the present invention.

Reference is now made to FIG. 2, which is a block diagram showing circuitry contained inside implant 24, in accordance with some embodiments of the present invention. Implant 24 comprises an antenna 34, configured to, by drawing energy from the magnetic field generated by the external unit, provide a main supply voltage. Implant 24 further comprises a capacitive pressure sensor 22, configured to vary its capacitance in response to the ambient pressure within the heart of subject 30 (i.e., the subject's intracardiac pressure). In response to control signals 48 from a logic processing unit (LPU) 40, a voltage regulator 46 converts a high voltage supply, which is derived from the main supply voltage, into a direct current (DC) sensor-supply voltage, which supplies sensor 22. Voltage regulator 46 requires a certain minimum supply voltage in order to effectively supply voltage to the sensor. For example, in some embodiments, voltage regulator 46 requires at least 15.5 V. (Since this threshold is relatively high, relative to respective voltages required by other components of implant 24, the voltage regulator supply voltage is referred to as a high voltage supply.) Voltage regulator 46 and sensor 22 may be collectively referred to as "operational circuitry."

Implant 24 further comprises modulating circuitry that modulates the load of antenna 34. For example, as shown in FIG. 2, the modulating circuitry may comprise an inputselecting-and-converting unit 36, LPU 40, and a modulation switch 42. These components will now be described.

Input-selecting-and-converting unit 36 comprises conversion circuitry, which generates an output having a property that is a function of the capacitance that is input to the circuitry. For example, as shown in the figure, the conversion circuitry may comprise a capacitance-to-frequency converter 44. Converter 44 is an oscillator whose oscillation frequency depends on the capacitance that is input to the converter, such that the converter outputs a "sensor clock out" clock signal whose frequency is a function of the input. Stated differently, converter 44 converts the input capacitance into an output frequency.

Input-selecting-and-converting unit 36 further comprises an analog selector 72 configured to, in response to control signals 70 delivered over control lines from LPU 40, select an input to converter 44. FIG. 2 shows several possible inputs, as follows:

(i) The capacitance of sensor 22 may be input to converter 44, such that converter 44 converts the capacitance of the sensor into the output frequency.

(ii) The capacitance of a reference capacitor 26 may be input to converter 44, such that the converter converts the capacitance of the reference capacitor into the output frequency. (The function of reference capacitor 26 is described below, with reference to FIG. 4.)

(iii) The capacitance of one or more calibration capacitors "Cref" may be input to converter 44, such that the converter converts the capacitance of the reference capacitor(s) into the output frequency. (The function of the calibration capacitors is described below, with reference to FIG. 4.)

In response to the "sensor clock out" signal, LPU 40 modulates the load of the antenna, by alternatingly connecting current-drawing circuitry to, and disconnecting the current-drawing circuitry from, the main supply voltage. When the current-drawing circuitry is connected to the main supply voltage, the load of the antenna is increased.

Conversely, when the current-drawing circuitry is disconnected from the main supply voltage, the load of the antenna is decreased. The modulation in the load of the antenna causes variations in the amount of energy from the magnetic field consumed by the implant. The external unit senses these variations, and computes, based on the variations, the input to converter 44. Thus, for example, LPU 40 may modulate the load of the antenna such as to indicate to the external unit the capacitance of—and hence, the pressure sensed by—sensor 22. The modulation in the load of the antenna also cause the main supply voltage to vary between a first, higher value, and a second, lower value. That is, when the current-drawing circuitry is disconnected from the main supply voltage, the main supply voltage has the first, higher value; conversely, when the current-drawing circuitry is connected to the main supply voltage, the main supply voltage has the second, lower value.

In some embodiments, the current-drawing circuitry comprises at least part of the modulating circuitry. In other words, in some embodiments, the modulating circuitry modulates the load of the antenna by alternatingly connecting the modulating circuitry to, and disconnecting the modulating circuitry from, the main supply voltage. For example, in the embodiment shown in FIG. 2, LPU 40 modulates the load of the antenna by alternatingly connecting itself to, and disconnecting itself from, the main supply voltage, by controlling a modulation switch 42. In particular, by closing switch 42, LPU 40 increases the load of the antenna by connecting the LPU (and/or the input-selecting-and-converting unit) to the main supply voltage; conversely, by opening the switch, LPU 40 decreases the load of the antenna by disconnecting the LPU (and/or the input-selecting-and-converting unit) from the main supply voltage.

Figure 3A:
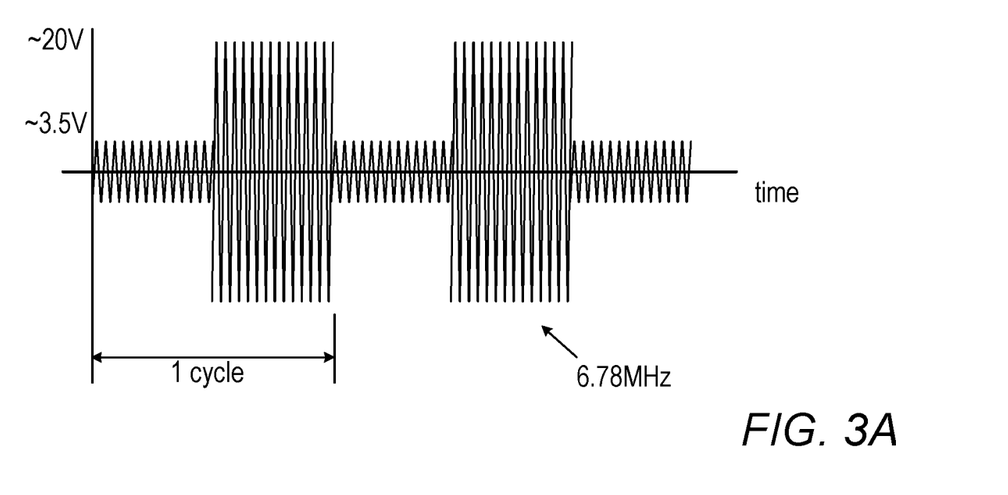
FIGS. 3A-B show respective example voltage waveforms, in accordance with some embodiments of the present invention.
Figure 3B:
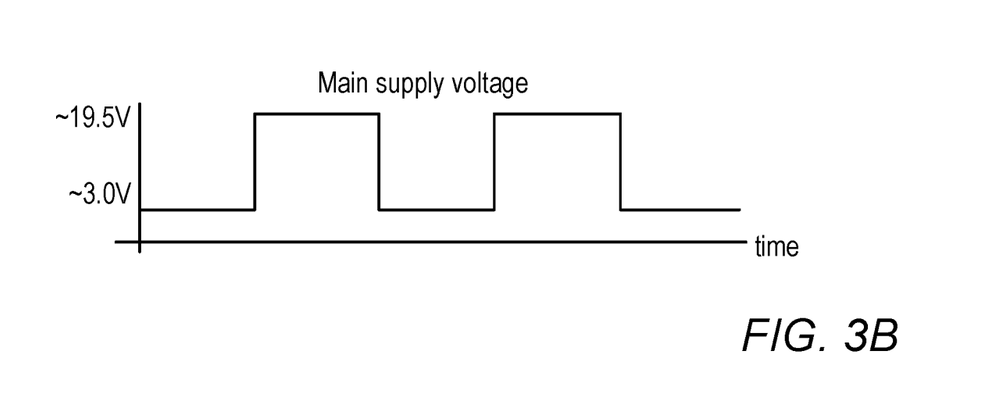

Reference is now additionally made to FIGS. 3A-B, which show respective example voltage waveforms, in accordance with some embodiments of the present invention. FIG. 3A shows an example waveform for the voltage across antenna 34, i.e., the output voltage of the antenna. As shown in the figure, the voltage oscillates at a characteristic frequency of, for example, 6.78 MHz, which is the frequency of the magnetic field generated by external unit 32. This output voltage of antenna 34 is modulated with an outer modulating envelope that is established by the controlling of switch 42 by LPU 40. The information contained in the feedback provided by the antenna is a function of the number and timing of the "cycles" of load modulation (and hence, voltage variation), one such cycle being labelled in FIG. 3A. A diode Dext1, shown in FIG. 2, detects the envelope, thus deriving, from the voltage across the antenna, the main supply voltage shown in FIG. 3B.

In the example shown in FIG. 3A, the threshold supply voltage for the voltage regulator is assumed to be approximately 15.5 V, and correspondingly, the amplitude of the voltage across the antenna varies between approximately 3.5 V and 20 V. Due to a small voltage drop across diode Dext1, the amplitude of the main supply voltage, as shown in FIG. 3B, varies between approximately 3 V and 19.5 V. (It is again noted that the voltage values in FIGS. 3A-B are provided by way of example only.)

For further clarity, the variations in the main supply voltage are now explained in more detail.

Antenna 34 may be modelled, simplistically, as an input voltage source providing an input voltage, and facing a particular output impedance. Hence, the more current flows across the antenna, the lower the output voltage of the antenna (shown in FIG. 3A) will be, due to a drop in voltage as current flows across the output impedance. When switch 42 is open, the load of the antenna is relatively small, such that relatively little current flows across the antenna; hence, the output voltage of the antenna is close to the input voltage. On the other hand, when switch 42 is closed, the load of the antenna is increased, such that more current flows across the antenna. (For example, LPU 40 may consume a relatively large amount of current, such that, when the switch is closed and LPU is connected to the main supply voltage, there is a relatively large increase in current across the antenna.) Hence, when switch 42 is closed, the output voltage drops below (e.g., significantly below) the input voltage.

Typically, the circuitry within implant 24 further comprises a backup voltage source, such as a capacitor Cext3. When the switch is open and the main supply voltage has the first, higher value (e.g., 19.5 V), the backup voltage source derives a backup voltage from the main supply voltage. For example, Cext3 may derive the backup voltage, by charging. When the switch is closed and the main supply voltage has the second, lower value (e.g., 3 V), the backup voltage source supplies the backup voltage to the voltage regulator.

As noted above, if the opening of the modulation switch were to also disconnect the voltage regulator and sensor from the main supply voltage, the voltage across the antenna (and hence, the main supply voltage) would need to be significantly higher. For example, to ensure a threshold supply voltage of 15.5 V for the voltage regulator, the voltage across the antenna when loaded with the current-drawing circuitry would need to be approximately 20 V, and hence, the voltage across the antenna when unloaded might need to be approximately 40 V. (In contrast, in the example embodiment provided herein, the voltage across the antenna when unloaded is approximately 20 V.) To generate such high voltages, the antenna would need to be supplied with a large amount of energy. Moreover, the supply of approximately 20 V to the LPU—which does not need such a large voltage, and which consumes a relatively large amount of current (e.g., 300 mAmp)—would lead to a large amount of excess power consumption. Hence, the placement of the modulation switch as shown in FIG. 2 is advantageous, in that (i) the voltage across the antenna may be relatively low (e.g., less than 22 V, such as approximately 20 V, as shown in FIG. 3B) when the current-drawing circuitry is disconnected from the main supply voltage, and/or (ii) when the current-drawing circuitry is connected to the main supply voltage, a much lower voltage—e.g., less than 5 V, such as approximately 3 V, as shown in FIG. 3B—may be supplied to the LPU.

It is noted that apparatus and techniques described herein may be applied to any alternative form of operational circuitry, any alternative form of modulating circuitry, and/or any alternative form of current-drawing circuitry. In other words, the scope of the present invention is not limited to the particular embodiments described herein, but rather, includes any relevant application in which there is a need to power both a relatively-high-voltage consumer (referred to herein as operational circuitry) and a lower-voltage-but-relatively-high-current consumer (referred to herein as current-drawing circuitry), while achieving sufficient antenna-modulation depth. For example, although the present description generally relates to sensor 22 as a capacitive pressure sensor, it is noted that the principles described herein may be applied to operational circuitry that comprises any type of sensor that is configured to sense any type of parameter. Similarly, the principles described herein may be applied to a sensor that is implanted in some portion of the anatomy other than the heart, to a sensor that is not implanted at all, as well as to operational circuitry that does not include a sensor at all.

Embodiments of the present invention also facilitate the operation of the current-drawing circuitry, even while the current-drawing circuitry is disconnected from the main supply voltage. For example, as shown in FIG. 2, the LPU may operate on a DC voltage Vcc that is supplied by a low dropoff oscillator (LDO) 38, which rectifies and regulates the main supply voltage. When switch 42 is open, LDO 38 is disconnected from the main supply voltage. Hence, to facilitate the operation of the LPU (and/or the input-selecting-and-converting unit) even while the switch is open, a second backup voltage source derives a second backup voltage from the main supply voltage, and, while the switch is open, supplies the second backup voltage to the LDO. For example, while the switch is closed, a capacitor Cext1 may charge, and subsequently, while the switch is open, supply voltage to the LDO. (Hence, LDO 38 is analogous to voltage regulator 46, while the second backup voltage source—e.g., Cext1—is analogous to the first backup voltage source—e.g., Cext3. While the switch is closed, the first backup voltage source supplies the voltage regulator, and while the switch is open, the second backup voltage source supplies the LDO.)

It is noted that the scope of the present invention includes the use of a backup voltage source for supplying voltage to the operational circuitry, as described above, even without the use of a backup voltage source for supplying voltage to the current-drawing circuitry. Similarly, the scope of the present invention includes the use of a backup voltage source for supplying voltage to the current-drawing circuitry, as described above, even without the use of a backup voltage source for supplying voltage to the operational circuitry.

In some embodiments, implant 24 further comprises a voltage clamper 50, which reduces variations in the second value of the main supply voltage that are caused by variations in the amount of current drawn by the current-drawing circuitry. For example, LPU 40 may draw varying amounts of current, depending on the current mode of operation of the LPU. Hence, without voltage clamper 50, the second value of the main supply voltage would vary, depending on the current mode of operation of the LPU. To reduce this variation, the voltage clamper draws an amount of current that varies inversely with the amount of current drawn by the LPU, such that, for example, the total amount of current drawn by the LPU and voltage clamper together, while the switch is closed, is constant. The voltage clamper may comprise, for example, a Zener diode.

Various other components of implant 24 are shown in FIG. 2, as follows:

(i) A diode Dext2 inhibits the discharging of Cext3, except for the purpose of supplying the voltage regulator.

(ii) A diode DZext1 provides overvoltage protection.

(iii) A capacitor Cext2 filters out noise from the voltage Vcc.

(iv) A capacitor Cext4 stabilizes the DC voltage supplied to the sensor.

(v) A "main clock/data in" signal, which is derived from the raw signal received from the external unit, provides a clock signal to the LPU, and further communicates data from the external unit. For example, via the "data in" signal, the external unit may request particular information from the LPU, which the LPU then provides, e.g., by selecting the appropriate input to capacitance-to-frequency converter 44, and then modulating the load of the antenna in response to the "sensor clock out" signal, as described above. The "main clock/data in" signal passes though a buffer 56, which adjusts the voltage of the signal to a level that is appropriate for the LPU.

(vi) An internal oscillator provides a clock signal to the LPU while the external unit is not transmitting.

(vii) A programmable resonance capacitor array 58 (depicted in FIG. 2, for simplicity, by only one capacitor) tunes the resonance capacitor in antenna 34, in response to signals 60.

(viii) A buffer 52 adjusts the voltage of the switch-controlling signal from the LPU to a level that is appropriate for switch 42.

(ix) A buffer 54 provides an indication to the LPU in the event that the voltage supply to voltage regulator 46 is not high enough. In response to the indication, the LPU communicates a signal to the external unit.

Figure 4:
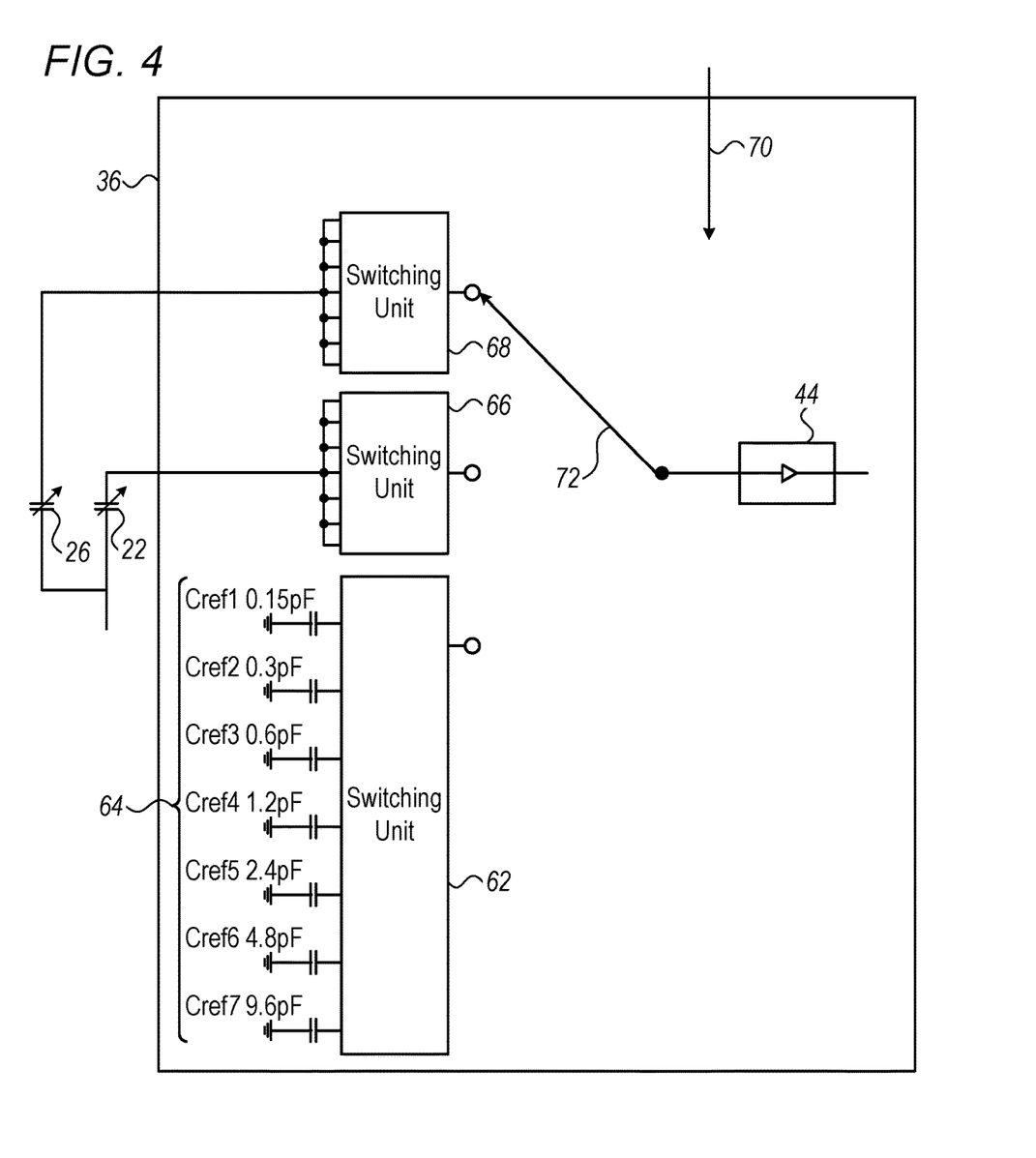
FIG. 4 is a block diagram that schematically illustrates an input-selecting-and-converting unit, in accordance with some embodiments of the present invention.

Reference is now made to FIG. 4, which is a schematic illustration of input-selecting-and-converting unit 36, in accordance with some embodiments of the present invention. FIG. 4 shows several aspects of unit 36 that are not shown in FIG. 2. In particular, FIG. 4 shows a set 64 of calibration capacitors, a first switching unit 62, a second switching unit 66, and a third switching unit 68. (Set 64 is roughly indicated in FIG. 2 by a single capacitor symbol labeled "Cref," while the switching units are not shown in FIG. 2.)

Set 64 is used to calibrate the conversion circuitry in converter 44, i.e., set 64 is used to ascertain the manner in which the frequency of the "sensor clock out" signal at the output of converter 44 varies as a function of the input capacitance to the converter. Switching unit 62 has multiple first-switching-unit settings that connect respective subsets of the calibration capacitors to the conversion circuitry. For example, switching unit 62 may comprise multiple switches, and for each first-switching-unit setting, a respective subset of the switches may be closed, thus connecting a respective subset of the calibration capacitors to the converter. Hence, by varying the setting of switching unit 62, various input capacitances may be obtained. For each input capacitance, the frequency of the output signal from the converter is recorded, such that the "input-capacitance-to-output-frequency" mapping of the converter is obtained. Subsequently, the inverse of the mapping may be used to compute the capacitance of sensor 22, given the output of the converter.

For example, FIG. 4 shows seven calibration capacitors: (i) Cref1, having a capacitance of 0.15 pF, (ii) Cref2, having a capacitance of 0.3 pF, (iii) Cref3, having a capacitance of 0.6 pF, (iv) Cref4, having a capacitance of 1.2 pF, (v) Cref5, having a capacitance of 2.4 pF, (vi) Cref6, having a capacitance of 4.8 pF, and (vii) Cref1, having a capacitance of 9.6 pF. By connecting various subsets of capacitors Cref1, Cref2, Cref3, Cref4, Cref5, Cref6, and Cref7l to the converter, various input capacitances may be obtained.

Typically, the above-described calibration procedure is performed prior to every capacitance/pressure measurement, since fluctuations in body temperature and/or voltage supply Vcc, and/or aging of the system, may influence the manner in which the output of the converter depends on the input capacitance.

A challenge inherent in using the above calibration technique is that the switching unit typically has a further setting-dependent effect on the output of converter 44, beyond the mere selection of input capacitance. For example, the resistance of switching unit 62 may vary depending on the selected setting of the switching unit, such that each of the first-switching-unit settings has a respective first-switching-unit resistive effect on the output of converter 44. In other words, the respective outputs observed during calibration are a function not only of the respective input capacitances, but also of the respective "input resistances" provided by the first switching unit.

Second switching unit 66, which is connected to the sensor, addresses the above challenge. Second switching unit 66 has multiple second-switching-unit settings that (i) connect the sensor to the converter, and (ii) have respective second-switching-unit effects on the output of the converter that are the same as the first-switching-unit effects. In other words, the second switching unit is effectively a duplicate of the first switching unit. Unlike unit 62, however, unit 66 always connects the same capacitance—that of sensor 22—to the input of converter 44, regardless of the selected setting. Hence, by controlling the second switching unit, the effect (e.g., the resistive effect) of the second switching unit may be "matched" to an effect (e.g., a resistive effect) provided by the first switching unit during calibration, thus allowing the capacitance of sensor 22 to be accurately computed from the output of the converter. An implementation of this will now be described.

As described above with reference to FIG. 2, LPU 40, via control signals 70, controls analog selector 72, which varies the source of the input to the converter. Furthermore, LPU 40 (via control signals 70), and/or other circuitry in the implant, controls switching units 62 and 66. In particular, during calibration, the first switching unit is set to each of the first-switching-unit settings, thus driving the conversion circuitry to generate multiple calibration outputs, such that the correspondence between the calibration outputs and the first-switching-unit settings may be ascertained. For example, the external unit may store a "correspondence table" (or other analogous data-storage object) in which each first-switching-unit setting is "mapped" to a particular output.

Subsequently, during the "real-time" sensing of sensor 22, the analog selector connects the converter to second switching unit 66. The LPU, and/or other circuitry, in response to instructions from the external unit, then sets the second switching unit to one or more of the second-switching-unit settings, thus varying the input resistance to the converter. By varying the setting of the second switching unit, the LPU drives the converter to generate one or more sensing outputs, which the LPU then communicates to the external unit. In response to the sensing outputs and the correspondence that was ascertained from the calibration, the external unit computes the capacitance of the sensor (and hence, the pressure sensed by the sensor).

For example, the LPU may vary the setting of the second switching unit, i.e., set the second switching unit to another one of the second-switching-unit settings, until (as determined by the external unit) the output converges to a calibration output that corresponds to the current setting of the second switching unit. For example, the LPU may vary the setting of the second switching unit until (i) the difference between the sensing output and a particular calibration output is within a predefined threshold (and/or the difference between the sensing output and the particular calibration output is a minimum—i.e., it is locally or globally less than respective differences between the sensing output and other calibration outputs), and (ii) per the correspondence that was ascertained during calibration, the particular calibration output corresponds to the current setting of the second switching unit.

To further clarify the above description, some notation will now be introduced, and the above description will then be repeated, using the notation.

(i) $\{S1\_i\}$, for $i=1 \ldots N$, is the set of first-switching-unit settings S1, each particular setting $S1\_i$ having a respective input capacitance $C\_i$ and a respective input resistance $R\_i$.

(ii) $\{O\_i\}$, for $i=1 \ldots N$, is the set of calibration outputs obtained during calibration, each particular output $O\_i$ being obtained for a respective particular setting $S1\_i$.

(iii) $\{S2\_i\}$, for $i=1 \ldots N$, is the set of second-switching-unit settings S2, each particular setting $S2\_i$ having a respective input resistance $R\_i$ that is the same as the input resistance of a particular $S1\_i$.

(iv) $C\_s$ is the (unknown) capacitance of the sensor.

During calibration, the correspondence between $\{O\_i\}$ and $\{S1\_i\}$ is ascertained, and the external unit stores the correspondence. For example, the external unit may store a correspondence table having a form similar to Table 1 below:

TABLE 1

| | |
|---|---|
| S1_1 | O_1 |
| S1_2 | O_2 |
| S1_3 | O_3 |
| ... | ... |
| S1_N | O_N |

Subsequently, during real-time, the setting of the second switching unit is varied over one or more of settings $\{S2\_i\}$, until, for example, (a) the difference between the sensing output from the converter and a particular calibration output $O\_j$ is within a predefined threshold, and/or is a local or global minimum, and (b) O_j corresponds to the current setting of the second switching unit. C_s is then computed to be equal to, or approximately equal to, C_j, the input capacitance of S1_j.

For example, with reference to Table 1 above, if the sensing output from the converter is within a predefined threshold of O_2, and the current setting of the second switching unit is S2_2 (which has the same input resistance as S1_2, to which O_2 corresponds), C_s is computed to be equal to, or approximately equal to, C_2.

Figure 5:
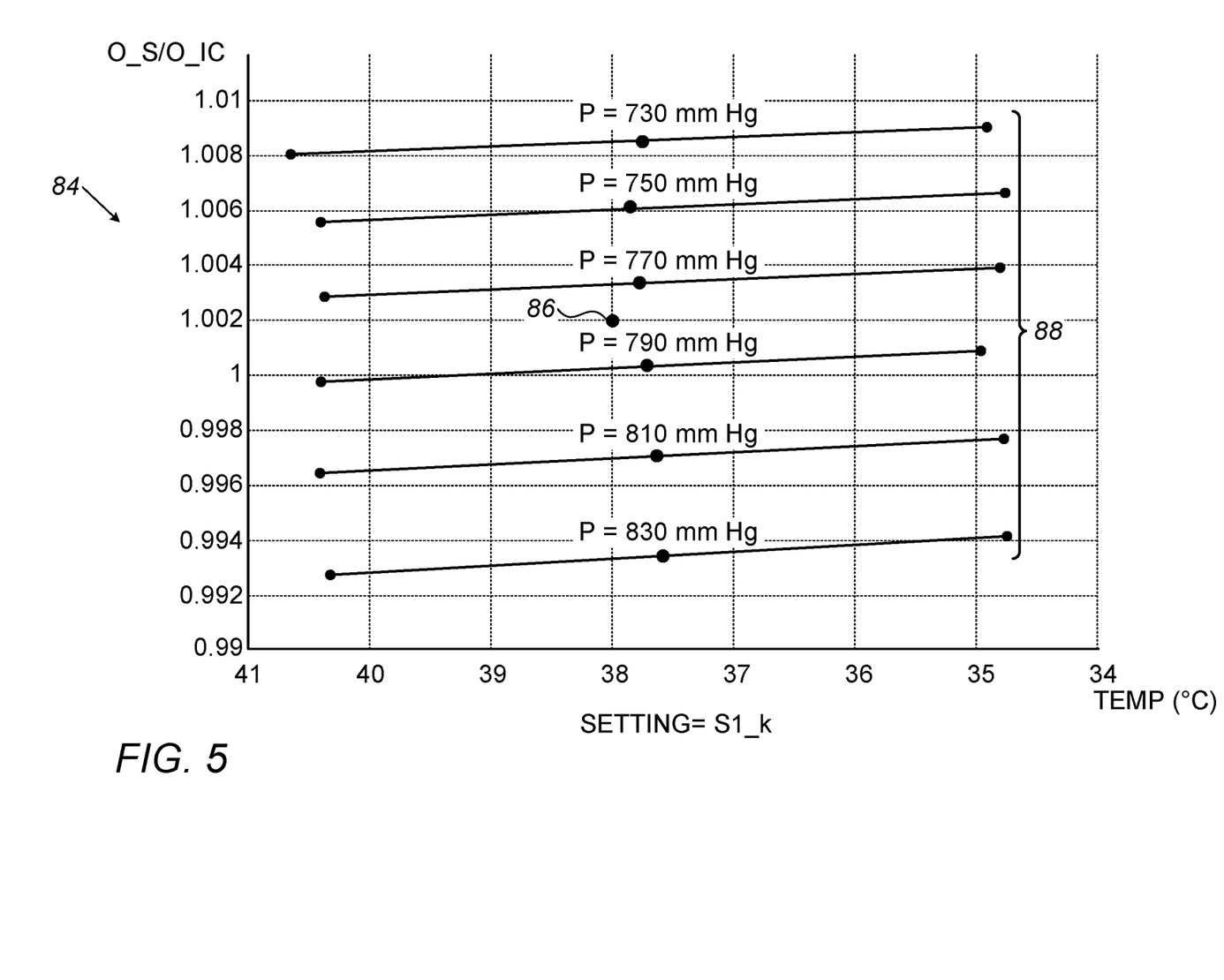
FIG. 5 shows an example calibration map, used in accordance with some embodiments of the present invention.

Reference is now made to FIG. 5, which shows an example calibration map 84, used in accordance with some embodiments of the present invention.

In some embodiments, prior to implanting the sensor, an alternative calibration to the above-described calibration is performed, whereby one or more calibration maps such as calibration map 84 are constructed, by obtaining various outputs of capacitance-to-frequency converter 44 while controlling the ambient temperature and pressure. It is noted that the calibration data shown in FIG. 5 roughly corresponds to real calibration data obtained by the inventors of the present application. (Typically, the calibration procedure described below is performed separately for each individual sensor.)

Each of the calibration maps is constructed for a respective setting of the first switching unit; for example, calibration map 84 corresponds to a particular setting S1_k of the first switching unit. Each calibration map includes (i) various first calibration outputs (O_IC) of the conversion circuitry that are output responsively to the known input capacitance ("IC") corresponding to the setting of the first switching unit, and (ii) various second calibration outputs (O_S) of the conversion circuitry that are output responsively to input from the pressure sensor ("S"). The first calibration outputs are measured for different respective ambient temperatures, while the second calibration outputs are measured for different respective ambient temperatures and ambient pressures. (In some embodiments, the first calibration outputs are also measured for different respective controlled ambient pressures. In other embodiments, the first calibration outputs do not vary with ambient pressure, and hence, a first calibration output measured for one particular ambient pressure may be extrapolated to other ambient pressures.) As further described below, the first and second calibration outputs are later used in real-time, while the sensor is implanted, to ascertain the ambient pressure within the subject.

The outputs from the conversion circuitry are typically expressed in units of frequency, such as in units of "counts," referring to the number of peaks in the output signal counted within a particular window of time.

In some embodiments, as shown in FIG. 5, each calibration map includes the ratio O_S/O_IC plotted against temperature (Temp) in degrees Celsius (C), for a plurality of ambient pressures P in mm Hg. (It is noted that the temperatures are decreasing from left to right.) Hence, each calibration map includes a plurality of temperature-sensitivity curves 88, each of which reflects the sensitivity of the conversion circuitry, the sensor, and/or the switching units to temperature at a different respective pressure. Each data point on a particular curve 88 is obtained during calibration, by (i) measuring O_S for a particular ambient pressure and temperature of interest, (ii) measuring O_IC for the same particular ambient temperature (and, if the first calibration output is deemed to be sensitive to the ambient pressure, also for the same particular ambient pressure), and (iii) subsequently, computing the ratio O_S/O_IC (or alternatively, O_IC/O_S).

Subsequently, in real-time, the unknown ambient pressure within the subject is ascertained, as follows:

(i) If there are a plurality of calibration maps, one of the calibration maps, corresponding to a given one of the first-switching-unit settings (and hence, a given one of the known input capacitances of the calibration capacitors), is selected, as further described below.

(ii) The ambient temperature is measured.

(iii) While the first switching unit is set to the given one of the first-switching-unit settings, and the conversion circuitry is connected to the first switching unit, a first real-time output of the conversion circuitry, O_IC_RT, which is output responsively to the given one of the input capacitances, is measured. For example, if calibration map 84 as shown in FIG. 5 is the selected calibration map, O_IC_RT is measured while the first switching unit is set to S1_k.

(iv) The conversion circuitry is connected to the pressure sensor (e.g., via the second switching unit), and a second real-time output of the conversion circuitry, O_S_RT, which is output responsively to the input from the pressure sensor, is measured.

(v) The unknown ambient pressure is ascertained, based on O_IC_RT, O_S_RT, the measured ambient temperature, and the calibration information contained in the calibration map. For example, this may be done by comparing the ratio between the first and second real-time outputs to the ratios obtained during calibration. A particular example is shown in FIG. 5, in which point 86 corresponds to a hypothetical real-time data point of (38 C, 1.002). Since this point lies approximately halfway between the temperature-sensitivity curve for P=770 and the temperature-sensitivity curve for P=790, it may be ascertained that the ambient pressure is approximately 780. (In practice, interpolation is used to precisely compute the ambient pressure.)

It is noted that the above-described method could, in theory, be performed without the use of the calibration capacitors. Per such a hypothetical "naïve" method, during calibration, O_S would be measured for different ambient pressures and temperatures, and subsequently, the calibration data would be used to estimate the unknown ambient pressure, as described above. A problem with this hypothetical method, however, is that, as the inventors have observed, the temperature sensitivity of the conversion circuitry may be dependent on the voltage supplied to the implant. Thus, for example, even for the same ambient pressure sensed by the pressure sensor, and at the same ambient temperature, the frequency of the signal output by the conversion circuitry may vary with the supplied voltage. Consequently, a calibration map could not be reliably used, if the supplied voltage during real-time is different from the supplied voltage during calibration.

To overcome this challenge, the above-described method uses the calibration capacitors, which help "normalize" the calibration output across different supplied voltages. In particular, as the inventors have further observed, the ratio between O_S and O_IC is invariant to the supplied voltage, at least if the input capacitance from the calibration capacitors is approximately the same as the input capacitance from the sensor. In other words, even if O_S changes by a factor of k as the supplied voltage changes from a first value to a second value, O_IC will also change by a factor of k, such that the ratio between O_S and O_IC will remain the same. The above-described method thus helps overcome the temperature sensitivity of the conversion circuitry, more effectively than does the hypothetical naïve method.

Since, as described above, the ratio between O_S and O_IC is least variant to the supplied voltage if the two inputs are approximately the same, the desired calibration map typically corresponds to the input calibration capacitance that is closest to the current capacitance of the sensor. The desired calibration map is selected during a "pre-real-time" stage, typically immediately prior to the real-time ascertaining of the unknown ambient pressure. During pre-real-time, respective pairs of "calibration" and "sensor" outputs are obtained for one or more of the switching-unit settings for which calibration maps were obtained, and the minimum difference between the pairs is identified. The selected calibration map then corresponds to the minimum difference. This may be expressed in the following notation:

(i) For each first-switching-unit setting S1_i of the one or more of the switching-unit settings for which calibration maps were obtained, the output O_IC_i of the conversion circuitry is measured, and for the identical second-switching-unit setting S2_i, the output O_S_i of the conversion circuitry is measured.

(ii) The absolute difference D_i between each of the (O_IC_i, O_S_i) pairs is computed.

(iii) In response to D_j being a local or global minimum of all the {D_i}, or lower than a particular threshold, the calibration map corresponding to S1_j is selected.

It is emphasized that the second switching unit facilitates the selection of the most appropriate calibration map. If not for the second switching unit, it would be impossible, or at least very difficult, to identify the input calibration capacitance that is closest to the current capacitance of the sensor, since the first switching unit also affects the output of the conversion circuitry. (In other words, due to the effect of the first switching unit on O_IC, the fact that O_S_j is close to O_IC_j would not necessarily indicate that the capacitance of the sensor is close to the input calibration capacitance.) Since, however, the second switching unit is used, a small difference between the outputs indicates that the input capacitance of the sensor and the input capacitance of the calibration capacitors are approximately the same. Moreover, the second switching unit is also typically used during calibration, and during real-time. That is, during calibration, when constructing the respective calibration map for each S1_i, the second switching unit is set to S2_i, and during real-time, the second switching unit is set to the setting S2_j, which is identical to the selected setting S1_j.

Typically, the external unit drives the LPU to control the input to the conversion circuitry, in order to execute all of the above-described calibration, pre-real-time, and real-time tasks. The LPU then communicates the output from the conversion circuitry to the external unit, as described above. Hence, the external unit, alone or in combination with the LPU, may be referred to as an example embodiment of "control circuitry" that controls the execution of the various tasks described herein.

To measure the temperature within the implant, an internal temperature sensor (not shown in the figures) is used. Typically, the temperature sensor also inputs to the conversion circuitry, such that, to obtain a temperature reading, the external unit drives the LPU to connect the conversion circuitry to the temperature sensor, and the LPU then communicates the output from the conversion circuitry to the external unit. The temperature is thus measured in frequency units, such as units of counts, like other output from the conversion circuitry. (Nonetheless, to make FIG. 5 more readily understandable, the temperature axis in calibration map 84 is marked in units of degrees Celsius, rather than units of counts.)

Typically, as described above with reference to FIG. 2, the implant further comprises reference capacitor 26, the capacitance of which does not vary in response to the ambient pressure. Reference capacitor 26 allows for compensating for factors, other than pressure, that may affect the capacitance of the sensor. For example, as the sensor ages, the manner in which the capacitance of the sensor varies in response to variations in the ambient pressure may change. Alternatively or additionally, radiofrequency (RF) noise may affect the capacitance of the sensor. As further described hereinbelow with reference to FIGS. 6A-B, by manufacturing reference capacitor 26 at the same time, and from the same wafer, as sensor 22, with identical electrical connections, and placing the reference capacitor near the sensor within the heart, the reference capacitor can be made to respond to these factors in the same manner in which the sensor responds. Thus, outputs from the reference capacitor may be used to adjust the computation of the capacitance of the sensor, to compensate for the above-mentioned factors.

To facilitate the use of the reference capacitor as described above, third switching unit 68 is typically connected to the reference capacitor. Third switching unit 68 has multiple third-switching-unit settings that (i) connect the reference capacitor to the converter, and (ii) have respective third-switching-unit effects (e.g., resistive effects) on the output that are the same as the first-switching-unit effects. Hence, by varying the setting of the third switching unit, an accurate computation of the capacitance of the reference capacitor may be obtained, as described hereinabove for the second switching unit. The capacitance of the reference capacitor may then be used to more accurately compute the ambient pressure, based on the computed capacitance of the sensor.

Figure 6A:
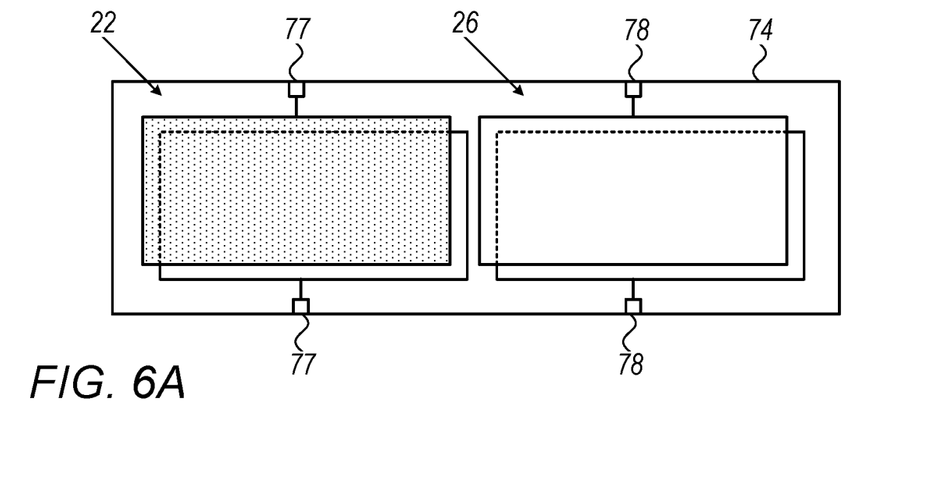
FIGS. 6A-B are schematic illustrations of a sensing capacitor and reference capacitor, in accordance with some embodiments of the present invention.
Figure 6B:
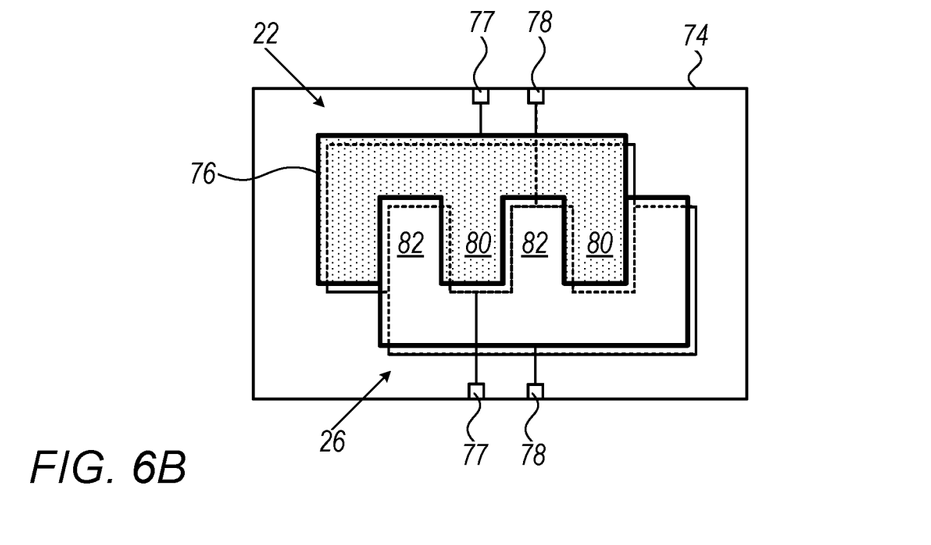

Reference is now made to FIGS. 6A-B, which are schematic illustrations of sensing capacitor 22 and reference capacitor 26, in accordance with some embodiments of the present invention. The sensing capacitor is formed from a first portion of a wafer 74, while the reference capacitor is formed from a second portion of wafer 74 that is adjacent to the first portion. Furthermore, the set 78 of electrical connections connected to the reference capacitor is identical to the set 77 of electrical connections connected to the sensing capacitor. The sets of electrical connections include, for example, wiring, vias connecting between conductive layers, and/or connection pads. The sets are "identical" to one another, in that the properties of one set—such as the material(s) from which the set is manufactured, and the geometrical layout of set—are the same as the properties of the other set.

The adjacency of the reference capacitor to the sensing capacitor on a shared wafer, along with the identical electrical connections, help the reference capacitor have very similar properties to those of the sensing capacitor, such that the respective capacitances of the capacitors are affected by age, RF noise, etc. in a similar manner. The only significant difference between the two capacitors is that while the sensing capacitor has at least one terminal 76 (e.g., capacitor plate) that is sensitive to the ambient pressure, the reference capacitor does not have any terminal that is sensitive to the ambient pressure.

As described hereinabove, the sensing capacitor and the reference capacitor are contained within implant 24, which is implanted in subject 30, such as within the subject's heart. In some embodiments, prior to implantation (e.g., prior to being placed within the implant), the two capacitors are separated (e.g., partly or completely detached) from one another. In any case, the two capacitors are typically placed near one another inside the implant, so that they are exposed to the same ambient environment within the subject.

In some embodiments, as shown in FIG. 6B, one or more portions 80 of the sensing capacitor protrude into the reference capacitor, and/or one or more portions 82 of the reference capacitor protrude into the sensing capacitor. For example, as shown in FIG. 6B, portions 82 of the reference capacitor may be interleaved with portions 80 of the sensing capacitor. The protruding of one capacitor into the other further helps the two capacitors have similar properties.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method for measuring ambient pressure using an implant that comprises a capacitive pressure sensor, a bank of capacitors, and capacitance-to-frequency conversion circuitry that generates an output signal whose frequency is indicative of an input capacitance connected thereto, the method comprising:
holding multiple calibration maps for the implant, wherein each calibration map calibrates a capacitance of the capacitive pressure sensor relative to a capacitance of a respective subset comprising one or more of the capacitors, each calibration map comprising multiple curves that specify, as a function of the ambient pressure and ambient temperature, a frequencies-ratio between (i) the frequency of the output signal produced when the capacitive pressure sensor is connected as the input capacitance and (ii) the frequency of the output signal produced when the respective subset of capacitors is connected as the input capacitance; and
at a measurement time, after the implant is implanted in a subject, estimating the ambient pressure at the implant, by:
acquiring a pressure measurement of the ambient pressure by connecting the capacitive pressure sensor to the capacitance-to-frequency conversion circuitry; and
applying one or more of the calibration maps to (i) the pressure measurement of the ambient pressure and to (ii) a temperature measurement of the ambient temperature at the implant.

2. The method according to claim 1, wherein estimating the ambient pressure comprises:
selecting a subset of the capacitors;
calculating the frequencies-ratio for the selected subset of capacitors; and
extracting the ambient pressure from a selected calibration map corresponding to the selected subset of capacitors, based on the measured ambient temperature.

3. The method according to claim 2, wherein selecting the subset of the capacitors comprises choosing a pre-specified subset whose capacitance is closest to a capacitance of the capacitive pressure sensor at the measurement time.

4. The method according to claim 2, wherein selecting the subset of the capacitors comprises adaptively choosing the subset whose capacitance is closest to a capacitance of the capacitive pressure sensor at the measurement time.

5. The method according to claim 2, wherein extracting the ambient pressure comprises interpolating between ambient pressure curves in the selected calibration map.

6. A system for measuring ambient pressure, the system comprising:
an implant, comprising:
a capacitive pressure sensor;
a bank of capacitors; and
capacitance-to-frequency conversion circuitry configured to generate an output signal whose frequency is indicative of an input capacitance connected thereto; and
control circuitry, configured to:
hold multiple calibration maps for the implant, wherein each calibration map calibrates a capacitance of the capacitive pressure sensor relative to a capacitance of a respective subset comprising one or more of the capacitors, each calibration map comprising multiple curves that specify, as a function of the ambient pressure and ambient temperature, a frequencies-ratio between (i) the frequency of the output signal produced when the capacitive pressure sensor is connected as the input capacitance and (ii) the frequency of the output signal produced when the respective subset of capacitors is connected as the input capacitance; and
at a measurement time, after the implant is implanted in a subject, estimate the ambient pressure at the implant, by:
acquiring a pressure measurement of the ambient pressure by connecting the capacitive pressure sensor to the capacitance-to-frequency conversion circuitry; and
applying one or more of the calibration maps to (i) the pressure measurement of the ambient pressure and to (ii) a temperature measurement of the ambient temperature at the implant.

7. The system according to claim 6, wherein the control circuitry is configured to estimate the ambient pressure by:
selecting a subset of the capacitors;
calculating the frequencies-ratio for the selected subset of capacitors; and
extracting the ambient pressure from a selected calibration map corresponding to the selected subset of capacitors, based on the measured ambient temperature.

8. The system according to claim 7, wherein the control circuitry is configured to select a pre-specified subset whose capacitance is closest to a capacitance of the capacitive pressure sensor at the measurement time.

9. The system according to claim 7, wherein the control circuitry is configured to adaptively choose the subset whose capacitance is closest to a capacitance of the capacitive pressure sensor at the measurement time.

10. The system according to claim 7, wherein the control circuitry is configured to extract the ambient pressure by interpolating between ambient pressure curves in the selected calibration map.

* * * * *